United States Patent [19]

Kurihara

[11] 4,175,547
[45] Nov. 27, 1979

[54] SPHYGMOMANOMETER AID

[76] Inventor: Sohachi Kurihara, 2-9 Daito 1-chome, Daito-ku, Tokyo, Japan

[21] Appl. No.: 820,035

[22] Filed: Jul. 28, 1977

[51] Int. Cl.² .............................................. A61B 5/02
[52] U.S. Cl. .................................................... 128/680
[58] Field of Search .................. 128/2.05 G, 2.05 A, 128/2.05 C, 2.05 M, 2.05 N, 2.05 Q; 73/748

[56] References Cited

U.S. PATENT DOCUMENTS

| 2,571,124 | 10/1951 | Farrand | 128/2.05 G |
| 4,005,701 | 6/1975 | Aisenberg | 128/2.05 G |

FOREIGN PATENT DOCUMENTS

| 2326378 | 11/1974 | Fed. Rep. of Germany | 128/2.05 G |
| 578182 | 9/1924 | France | 128/2.05 G |
| 1282926 | 12/1961 | France | 128/2.05 G |

*Primary Examiner*—Lee S. Cohen
*Attorney, Agent, or Firm*—Wenderoth, Lind & Ponack

[57] ABSTRACT

A sphygmomanometer aid includes a housing containing an electronic circuit including circuitry for sensing and indicating pulse sounds of a person whose blood pressures are to be measured and a board member pivotally connected to the housing and including structure for supporting a manometer gauge. The board member is set at the open position relative to the housing when in use, and receives and fixedly supports the manometer gauge, whereby a non-electronic sphygmomanometer can be used as an electronic blood pressure measuring device.

1 Claim, 7 Drawing Figures

PULSE DETECTION CIRCUIT

SPHYGMOMANOMETER AID

BACKGROUND OF THE INVENTION

This invention relates to a novel and useful auxiliary device for a sphygmomanometer of the aneroid type.

For measuring blood pressures, a pressure manometer of the aneroid or mercurial type and associated arm cuff have been used along with a stethoscope with which pulse sounds are heard to determine systolic and diastolic blood pressure readings.

For the purpose of making the blood pressure measurement easier and surer without requiring any proficiency, there have been developed and extensibly used electronic blood pressure measurement devices in which a transducer is used in place of stethoscope to sense pulse sounds in combination with an electronic circuit which indicates those pulse sounds by an indicator lamp or beeper.

Such electronic blood pressure measurement devices are useful and advantageous in that they allow unskilled persons to take blood pressure readings easily, as compared with conventional non-electronic sphygmomanometers. However, those electronic devices now on the market comprise a housing containing a manometer gauge and an electronic circuit, and an arm cuff, and are considerably expensive as compared with conventional non-electronic sphygmomanometers. In particular, an economic disadvantage is inevitable when an individual who already owns a conventional sphygmomanometer purchases an electronic blood pressure measurement device anew since the old unit would be a duplication.

As described above, for taking blood pressure readings, an arm cuff containing a sealed, impervious rubber bladder is wrapped around an upper arm of a person whose blood pressures are to be measured, followed by pressurizing of the bladder by a pumping means. The pressure is then reduced gradually during which changes in pulse sounds are heard with the use of a stethoscope to determine systolic and diastolic points, and corresponding pressure levels are read on a manometer of the aneroid or mercurial type connected to the rubber bladder.

In recent years with increasing concern about blood pressures among people in general, and also because of the fact that blood pressures are quite susceptible to mental tension at the time of measurement, it has become more common than ever to take blood pressure measurements outside of medical facilities, for example, at homes, offices or while travelling for health care guidance. For this reason, there has been a rapid and considerable increase in demands for so-called "Do-it-yourself" type home use blood pressure measurement units.

In this type of blood pressure measurement unit, an aneroid type manometer gauge is generally employed, and various new ideas have been incorporated to enable unskilled persons to use the unit easily and conveniently. To meet such requirements, there have been developed electronic blood pressure measurement units as referred to above. However, since those electronic units are expensive, in reality, conventional non-electronic sphygmomanometers are still sold in far greater proportions than electronic units.

The aneroid type manometer gauge primarily employed for conventional sphygmomanometers is preferably used in a vertical or nearly vertical position from the standpoint of accuracy on account of its construction. However, the manometer gauge has a configuration which does not permit standing in that preferable position by itself.

SUMMARY OF THE INVENTION

It is an object of the present invention to provide a simple auxiliary device which affords the conventional non-electronic sphygmomanometers the same functions as those of expensive electronic blood pressure measurement devices without being accompanied by the economic disadvantages mentioned above.

In accordance with the present invention, there is provided an auxiliary device for sphygmomanometers which not only affords conventional non-electronic sphygmomanometers the functions and performances equivalent to those of expensive electronic blood pressure measurement devices but also provides supporting of an aneroid type manometer gauge in a proper position to maintain accuracy.

BRIEF DESCRIPTION OF THE DRAWINGS

The accompanying drawings illustrate preferred embodiments of the present invention, in which.

PREFERRED EMBODIMENTS OF THE INVENTION

Now, the present invention will be explained in reference to embodiments shown in the accompanying drawings.

Figure 1:
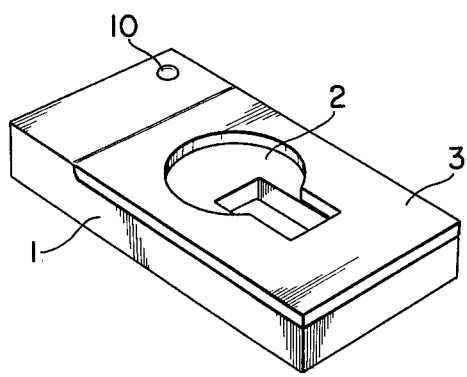
FIG. 1 shows a perspective view of the auxiliary device according to the present invention.
Figure 2:
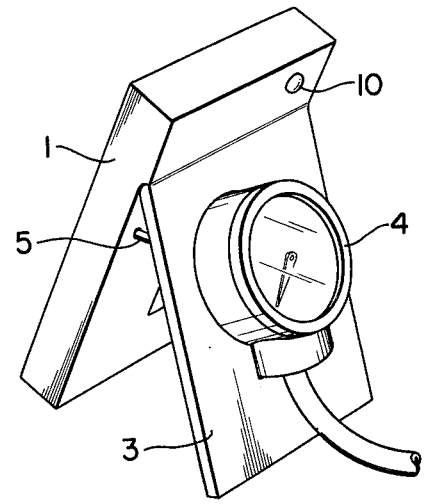
FIG. 2 is a perspective view of the same when in use.
Figure 3:
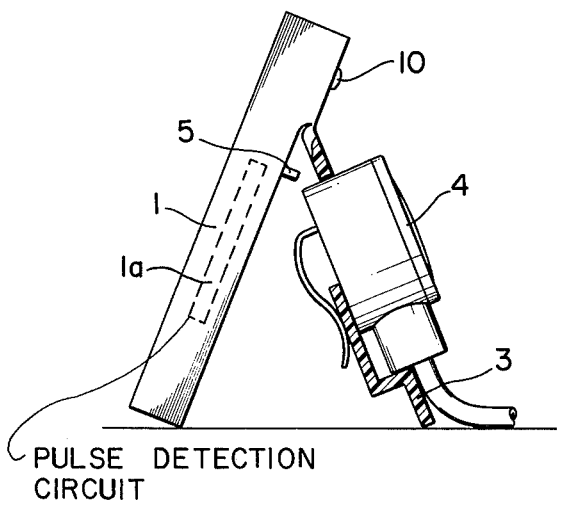
FIG. 3 shows a side view of the same when in use.

The auxiliary device of this invention comprises a housing 1 containing an electronic circuit provided with means for sensing pulses of a person whose blood pressures are to be measured and for indicating such pulses, and a board member 3 pivotally mounted to housing 1 so as to be set at open and closed positions and having a portion 2 to support a manometer gauge. The electronic circuit comprises an electronic circuit board 1a (shown schematically in FIG. 3) which is connected to a transducer applied to the person under measurement and amplifies pulses sensed and converted into electric signals by the transducer, and drives an indicating means employing a small electric lamp and/or a beeper. Housing 1 is provided with compartments to contain the electronic circuit board, a battery to operate the elecrtonic circuit, and the transducer which converts pulse sounds into electric signals.

Board member 3 is so constructed as to support an aneroid manometer gauge in a preferable position to maintain accuracy, and portion 2 for supporting the gauge is formed as a cut-out portion in board member 3. Upon use, board member 3 is set at the open postion and a manometer gauge 4 is put into the portion 2.

In embodiments illustrated in the accompanying drawings, the board member 3 is set at the open position upon use and it is set back to the closed position after use. A power switch 5 which is actuated in association with opening and closing of the board member 3 may be provided to prevent drainage of the battery resulting from inadvertent failure to turn it off after use.

Figure 5:
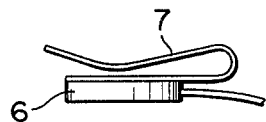
FIG. 5 shows a side view of a transducer.
Figure 6:
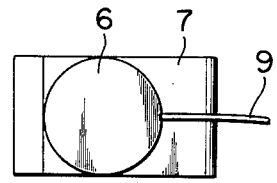
FIG. 6 is a plan view of the same.
Figure 7:
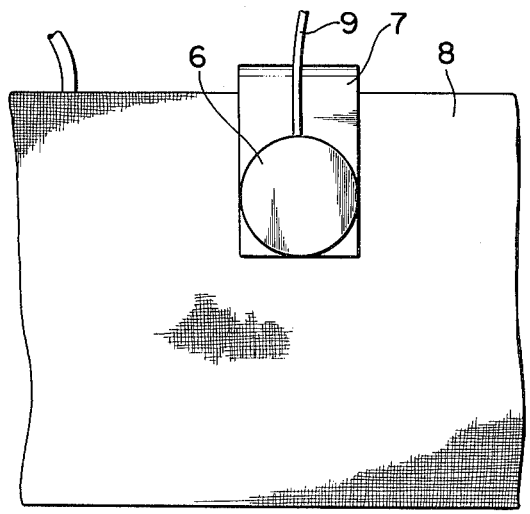
FIG. 7 is a plan view showing the use of the transducer.

Transducers of crystal or ceramic type are generally used for the device of the present invention. As shown in FIGS. 5 and 6, the transducer 6 has a clip means 7 and, upon use, it is fixed underneath an arm cuff 8 of a conventional non-electronic sphygmomanometer at a proper position by using clip means 7 as shown in FIG. 8. A connecting wire 9 of the transducer 6 is connected to a jack provided on the housing 1 by a conventional pin-plug. In the embodiments of the accompanying drawings, an indicator lamp 10 is provided on the housing 1 for indication of pulses.

Figure 4:
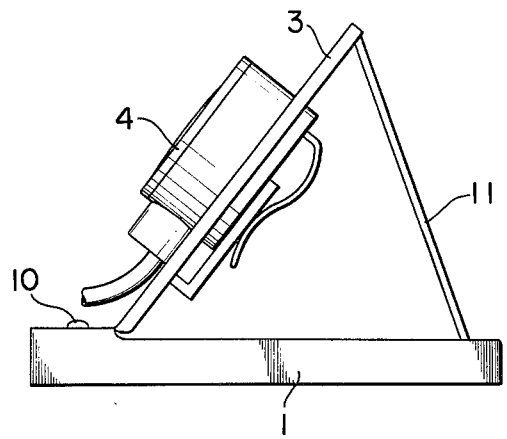
FIG. 4 is a side view of the device according to another embodiment of the invention.

While explanation has been given so far in conjunction with an embodiment wherein housing 1 and board member 3 are opened with respect to each other upon use so that housing 1 is allowed to stand in an inclined position, the device of this invention may also be constructed in such a manner that housing 1 is placed in a horizontal position and board member 3 is supported in an open position by a supporting member 11 as shown in FIG. 4. In this embodiment as well, of course, a manometer gauge 4 is placed on board member 3 and an indicator lamp 10 is provided on housing 1.

Now, when using the auxiliary device of the present invention, first the board member 3 is set at the open position and a manometer gauge 4 that came with a conventional non-electronic sphygmomanometer is placed at the portion 2 on the board member 3. After the arm cuff 8 of the conventional non-electronic unit containing a rubber bladder which is connected to manometer gauge 4 through a rubber tubing is wrapped around the upper arm of the person under measurement, the transducer 6 is placed underneath the arm cuff 8 at a proper position over the brachial artery, followed by connecting the connecting wire 9 to a jack on the housing 1. With this set up, blood pressure readings can be taken by operating a pumping means according to the same measurement procedures as in using an electronic blood pressure measurement device.

As described above, the auxiliary device of this invention makes it possible to use a non-electronic sphygmomanometer as an electronic blood pressure measurement unit, easily enabling a layman alone to take blood pressure readings and requiring no proficiency in the art. Furthermore, since with the use of the auxiliary device of this invention one can use a conventional non-electronic sphygmomanometer already owned as an electronic blood pressure measurement unit, not only is there brought about an economical advantage by making use of old unit without purchasing an expensive electronic unit, but also accurate measurement is ensured by supporting the manometer gauge in a proper position.

The auxiliary device of the present invention assumes a compact, flat, rectangular shape without any protrusions by closure of the board member when not in use to be easily stored or carried. Also, provision of a power switch associated with the movement of board member prevents drainage of the battery resulting from negligence in failing to turn off the battery after use.

I claim:

1. An auxiliary device for use with a conventional non-electronic sphygmomanometer of the type including an inflatable bladder which is wrapped around the arm of a patient and a manometer gauge connected to the inflatable bladder, said auxiliary device being employable with such conventional non-electronic sphygmomanometer for the electronic measurement of blood pressures of the patient, said auxiliary device comprising:
    a housing containing an electronic circuit including means for sensing and indicating pulses of a patient;
    a board member pivotally connected to said housing and movable with respect thereto between a closed position and an open inclined position;
    said board member including means for supporting a manometer gauge of a conventional non-electronic sphygmomanometer at an inclined orientation when said board member is in said open position;
    electronic transducer means, electrically and flexibly attached to said electronic circuit, for sensing pulses of the patient; and
    said transducer means having integral therewith means for attaching said transducer means to a cuff of an inflatable bladder of a conventional sphygmomanometer.

* * * * *